United States Patent [19]

Harandi

[11] Patent Number: 4,957,709

[45] Date of Patent: Sep. 18, 1990

[54] REACTOR SYSTEM FOR OLEFIN CONVERSION AND ETHERIFICATION

[75] Inventor: Mohsen N. Harandi, Lawrenceville, N.J.

[73] Assignee: Mobil Oil Corporation, New York, N.Y.

[21] Appl. No.: 419,927

[22] Filed: Oct. 11, 1989

Related U.S. Application Data

[63] Continuation-in-part of Ser. No. 189,450, May 2, 1988, Pat. No. 4,886,925.

[51] Int. Cl.$^5$ ............................ B01J 14/00; B01J 8/00
[52] U.S. Cl. ...................................... 422/134; 422/187; 422/189; 422/132; 422/131
[58] Field of Search ................ 585/310, 314, 315, 326, 585/329; 422/131, 132, 134, 141, 142, 145, 187, 189

[56] References Cited

U.S. PATENT DOCUMENTS

| | | | |
|---|---|---|---|
| 3,931,349 | 1/1976 | Kuo | 260/668 R |
| 3,960,978 | 6/1976 | Givens et al. | 260/683.15 R |
| 4,021,502 | 5/1977 | Plank et al. | 260/683.15 R |
| 4,404,414 | 9/1983 | Penick et al. | 585/469 |
| 4,456,779 | 6/1984 | Owen et al. | 585/415 |
| 4,511,747 | 4/1985 | Wright et al. | 585/415 |
| 4,542,252 | 9/1985 | Graziani et al. | 585/640 |
| 4,544,776 | 10/1985 | Osterburg et al. | 568/697 |
| 4,603,225 | 7/1986 | Colaianne et al. | 568/697 |
| 4,684,757 | 8/1987 | Avidan et al. | 585/331 |
| 4,746,761 | 5/1988 | Avidan et al. | 585/331 |
| 4,754,078 | 6/1988 | Vora et al. | 568/697 |
| 4,827,046 | 5/1989 | Harandi et al. | 585/310 |
| 4,830,635 | 5/1989 | Harandi et al. | 44/56 |

FOREIGN PATENT DOCUMENTS 8630430 12/1986 European Pat. Off.
0026041 1/1983 Fed. Rep. of Germany.

Primary Examiner—Chung K. Pak
Attorney, Agent, or Firm—Alexander J. McKillop; Charles J. Speciale; L. G. Wise

[57] ABSTRACT

An integrated reactor system for conversion of $C_2+$ normal olefins into tertiary-alkyl ethers and high octane gasoline. The system combines unit operations for olefins interconversion with etherification and conversion of unreacted alcohol and olefin in contact with acidic, shape selective metallosilicate zeolite catalyst.

4 Claims, 1 Drawing Sheet

REACTOR SYSTEM FOR OLEFIN CONVERSION AND ETHERIFICATION

REFERENCE TO COPENDING APPLICATION

This application is a continuation-in-part of U.S. patent application Ser. No. 07/189,450 filed May 2, 1988, now U.S. Pat. No. 4,886,925, incorporated herein by reference.

BACKGROUND OF THE INVENTION

This invention relates to a novel reactor system for production of liquid fuels from lower olefins. The invention particularly relates to integrated unit operations for production of tertiary alkyl ethers and high octane gasoline by interconversion of lower olefins and the conversion of olefins to higher hydrocarbons.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is new processes to produce high octane gasolines blended with lower aliphatic alkyl ethers as octane boosters and supplementary fuels. $C_5$–$C_7$ lower alkyl, tert-alkyl ethers, especially methyl t-butyl ether (MTBE) and t-amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiary-amyl methyl ether (MTBE). In these etherification processes a problem of major importance is that methanol is not totally converted and the separation of methanol from the etherification reaction product due to the proclivity of methanol to form a very dilute azeotropic mixture with hydrocarbons and the strong solubility of methanol in both water and hydrocarbons. Due largely to these factors, the cost associated with methanol separation and recycling in the etherification reaction represents approximately 30% of the cost of the total etherification process.

In U.S. Pat. No. 4,684,757 to Avidan et al. the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process of Avidan et al. converts oxygenate feedstock. The process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. Depending on various conditions of space velocity, temperature and pressure methanol, and lower oxygenates in general, can be converted in the presence of zeolite type catalyst to olefins which may then oligomerize to provide gasoline or distillate or be converted further to produce aromatics.

In another application of zeolite catalysis, at low pressure and high temperature light olefins can be interconverted or redistributed to produce higher olefins rich in isoalkenes.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using olefinic feedstocks for producing $C_5+$ gasoline, diesel fuel, etc. In addition to the basic work derived from ZSM-5 type zeolite catalyst, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$–$C_5$ alkenes. In U.S. Pat. Nos. 3,960,978 and 4,021,502, Plank Rosinski and Givens disclose conversion of $C_2$–$C_5$ olefins, alone or in admixture with paraffinic components into higher hydrocarbons over crystalline zeolites having controlled acidity. Garwood et al. have also contributed improved processing techniques to the MOGD system as in U.S. Pat. Nos. 4,150,062, 4,211,640 and 4,227,992. The conversion of olefins to gasoline using a fluidized catalyst bed is the subject of U.S. Pat. No. 4,746,762 (Avidan et al), incorporated herein by reference. Under conditions of moderate reaction severity, olefins are converted to predominantly gasoline boiling range products in a modification of the MOGD process known as Mobil Olefins to Gasoline (MOG).

An established process for the conversion of oxygenates to gasoline is the methanol to gasoline process, known as MTG. This process is described in U.S. Pat. No. 3,931,349 to Kuo, U.S. Pat. No. 4,404,414 to Penick et al. and in the publication by C. D. Chang, Catal. Rev.-Sci. Eng., 25, 1 (1983). These references are incorporated herein in their entirety Recognizing the limiting problems of the etherification processes to produce MTBE and TAME and the potential that resides in the general area of the chemistry of oxygenate and olefin conversion with zeolites to resolve those problems, several objectives of the instant invention have been established.

First, it is an object of the present invention to provide an integrated process and reactor system for the production of liquid fuel mixtures from olefin containing feedstock and lower alkyl alcohols by etherification and olefin conversion and interconversion reactions. It is another object of the present invention to provide a process for the production of liquid fuels of enhanced octane value containing MTBE and TAME.

SUMMARY OF THE INVENTION

The discovery has been made that the reactor means for interconverting lower olefins such as $C_2+$ olefins to produce higher lower olefins rich in iso-olefins can be advantageously integrated with other reactor means to produce tertiary alkyl ethers such as methyl tertiary alkyl ether (MTBE) and methyl tertiary amyl ether (TAME) and other reactor means to convert lower oxygenates and olefins to higher hydrocarbons. In the integrated process excess methanol used in the etherification reaction is not recovered and recycled to the etherification reaction but passed to an oxygenates and olefins or olefins and paraffins converion zone in contact with metallosilicate zeolite catalyst for conversion to liquid fuels or aromatics. Olefins from the interconversion step or the entire interconversion reaction effluent are used as feedstock to the etherification reaction either alone or in combination with another hydrocarbon feedstream rich in iso-alkenes.

In the preferred embodiment a multi-reactor system is provided for producing liquid fuel mixtures from olefin feedstock and lower alcohols by multistage etherification, olefin interconversion and oligomerization reactions comprising: first reactor means for contacting an olefinic hydrocarbon feedstock rich in $C_2+$ n-alkenes with acidic, medium pore metallosilicate catalyst in an olefin interconversion zone under mild olefin interconversion conditions to produce a reactor first effluent comprising $C_4$-$C_6$ alkenes rich in isoalkenes, $C_7+$ olefinic gasoline boiling range hydrocarbons and unconverted hydrocarbons; first separation means for separating the first reactor effluent to provide a first effluent stream comprising $C_4$-$C_6$ alkenes rich in isoalkenes, a second effluent stream comprising $C_7+$ olefinic gasoline boiling range hydrocarbons and a third efflent stream comprising unconverted hydrocarbons; second reactor means for reacting said first effluent stream with lower aliphatic alcohol in the presence of an acid etherification catalyst under reaction conditions effective to produce a mixture of tertiary-alkyl ethers; second separation means for reeovering a liquid product stream rich in tertiary-alkyl ethers and recovering a light hydrocarbon fraction containing unreacted alkenes from the reaction effluent of the first reactor means along with unreacted alcohol; and third reactor means for contacting the recovered light hydrocarbon and alcohol fraction from the second separation means concurrently with the second and third effluent streams from the first separation means with an acid oligomerization and oxygenate conversion catalyst to convert at least a portion of said unreacted alkenes and alcohol to heavier liquid hydrocarbon product, including $C_{10}+$ distillate range hydrocarbons, aromatics and/or $C_5$-$C_9$ gasoline boiling range hydrocarbons.

DESCRIPTION OF SPECIFIC EMBODIMENTS

Figure 1:
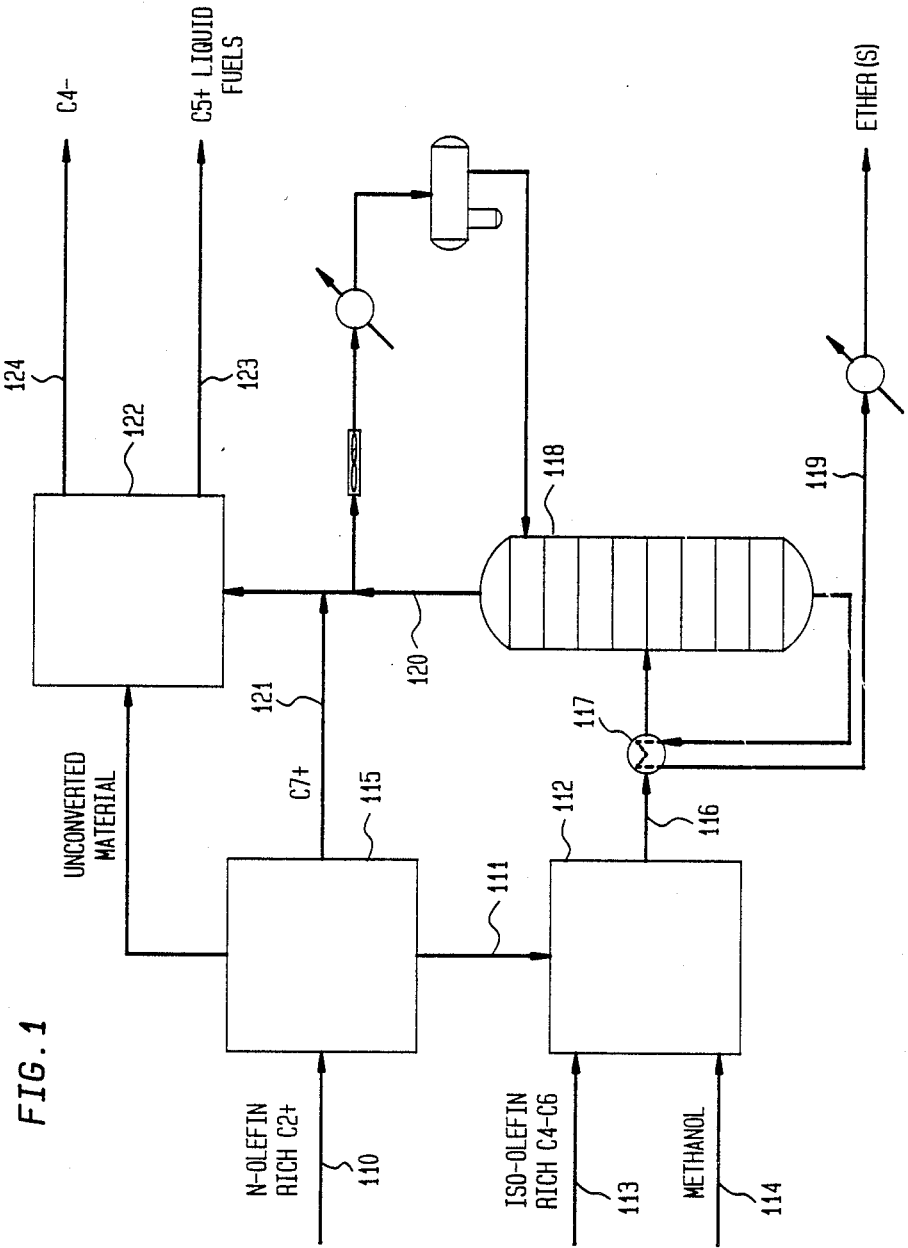
FIG. 1 is a schematic drawing of the multi-reactor system of the present invention.

In the preferred embodiments of this invention methanol is reacted with a hydrocarbon feedstock containing olefins, and particularly isoolefins such as isobutene, to produce methyl tertiary butyl ethers and other ethers. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites such as Zeolite Beta. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The major reaction units are operatively connected in a synergistic combination whereby etherification reaction effluent is utilized to provide reactive olefins for zeolite catalyzed conversion in conjunction with olefin interconversion products. Isomerization, oligomerization, alkylation and aromatizations reactions may be controlled in the acidic zeolite catalysis zone to obtain a desirable distribution of normally liquid hydrocarbons useful in making gasoline and/or distillate range fuels or aromatics such as BTX for petrochemical feedstock. Advantageously, at least a portion of the gasoline range hydrocarbons are recovered with $C_5+$ etherate octane enhancers useful in quality motor fuels. MTBE and TAME are preferred ethers. The $C_4$-$C_6$ alkene fraction from the olefin interconversion zone is utilized as etherification feedstock, optionally with fresh feedstock rich in $C_4$-$C_6$ iso-olefins.

The reaction of methanol with iso-butylene and isoamylenes at moderate conditions with a resin catalyst is known technology. Processes for producing and recovering MTBE and other methyl tertiary alkyl ethers from $C_4$-$C_7$ lsoolefins are known to those skilled in the art, such as disclosed in U.S. Pat. Nos. 4,788,365; 4,814,519; and 4,820,877 (Harandi et al), incorporated by reference.

Operating details for typical MOGD units are disclosed in U.S. Pat. Nos. 4,456,779; 4,497,968 (Owen et al.) and U.S. Pat. No. 4,433,185 (Tabak), incorporated herein by reference. In the process for catalytic conversion of oxygenate and/or olefins to heavier hydrocarbons by catalytic oligomerization using an acid crystalline zeolite, such as ZSM-5 type catalyst, process conditions can be varied to favor the formation of either gasoline, distillate, lube range products or aromatics. In the aforenoted MOGD process, light olefins are oligomerized to high molecular weight distillate range olefins over ZSM-5. In that process olefin molecular weight growth through a sequence of oligomerization and cracking reactions is thermodynamically forced at relatively high pressures of about 5600 kPa (800 psia) and relatively low temperatures of about 260° C. (500° F.). At much lower pressure and higher temperature, thermodynamics restrict the olefin distribution to low molecular weight. This is the basis for the olefin interconversion process, i.e., to operate under conditions where lower olefins, such as $C_2$-$C_4$ olefins can be converted to an equilibrium distribution of olefins with iso-butenes and iso-pentenes maximized. The olefin interconversion process as utilized in the present invention can use fixed bed, moving bed or fluid bed reactors containing zeolite type catalysts such as ZSM-5. Operating conditions encompass temperatures between 200° and 400° C. and low pressures, generally between 100 and 1500 kPa.

Optionally, conversion condition in the present invention may be controlled to favor the formation of aromatics, typified by the process known as M-2 Forming. Light aliphatic, paraffinic/olefinic feed can be converted under conditions described in U.S. Pat. No. 3,760,0242 to Cattanach, incorporated herein by reference. The operating conditions are temperatures from 300° to 750° C. and pressures from atmospheric to 3600 KPa (500 psig), preferably about 550° C. and 350 kPa. The reaction products comprise an effluent stream of light gases such as hydrogen and methane, unconverted light hydrocarbons and $C_5+$ aromatics.

The conversion of methanol and other alkanols, olefins and paraffins to gasoline, alkylated aromatics, and aromatics occurs under a broad range of operating conditions, but is preferably catalyzed by a crystalline-zeolite catalyst having acidic functionality. The preferred class of medium pore zeolite catalysts is characterized by a Constraint Index of 1 to 12 and a silica:alumina ratio of at least 12:1 and preferably higher e.g. 30:1, 70:1, 500:1, or even higher. Preferred zeolites which have the specified values of Constraint Index and silica:alumina ratio include zeolites ZSM-5, ZSM-11, ZSM-12, ZSM-35, and ZSM-48.

Referring to the drawing according to the instant invention, hydrocarbon stream 110 rich in $C_2+$ normal olefins is passed to an olefins interconversion zone containing acidic catalyst, preferably ZSM-5 of intermediate pore size, for the conversion of lower olefins to higher olefins rich in $C_4$–$C_6$ iso-olefins plus $C_7+$ olefinic gasoline and unconverted hydrocarbons. The $C_4$–$C_6$ stream 111 is passed to etherification zone together with a fresh iso-olefin $C_4$–$C_6$ stream 113 and methanol stream 114. The etherification zone effluent 116 is cooled in exchanger 117 and passed to debutanizer or depentanizer 118 where a hydrocarbon stream 119 rich in $C_5+$ ethers is separated and an overhead stream 120 containing unreacted methanol and olefins. The overhead stream, in conjunction with $C_7+$ olefinic stream 121 from interconversion zone 115 and, optionally, unreacted olefins containing interconversion light gas by-product from zone 115 are passed to oxygenates and olefins conversion zone 122 containing metallosilicate zeolite catalyst. Conversion zone 122 may be operated under oligomerization conditions and/or aromatizations conditions to convert methanol and olefins o olefins/paraffins to higher hydrocarbons containing distillate or aromatics-rich hydrocarbons. Preferably, $C_5+$ gasoline boiling range hydrocarbons 123 are produced rich in aromatics. Line 124 recovers $C_4$-hydrocarbon products.

While the invention has been described by reference to specific embodiments, there is no intent to limit the invention except as described in the following claims.

I claim:

1. A reactor system for producing liquid fuel mixtures from olefin-containing feedstock and lower alcohols by multistage etherification, olefin interconversion and oligomerization reactions comprising:
   first reactor means for contacting an olefinic hydrocarbon feedstock rich in $C_2+$ n-alkenes with acidic, medium pore metallosilicate catalyst in an olefin interconversion zone under mild olefin interconversion conditions to produce a reactor first effluent comprising $C_4$–$C_6$ alkenes rich in isoalkenes, $C_7+$ olefinic gasoline boiling range hydrocarbons and unconverted hydrocarbons;
   first separation means for separating the first reactor effluent to provide a first effluent stream comprising $C_4$–$C_6$ alkenes rich in isoalkenes, a second effluent stream comprising $C_7+$ olefinic gasoline boiling range hydrocarbons and a third effluent stream comprising unconverted hydrocarbons;
   second reactor, receivably connected to said first separation means, comprising means for reacting said first effluent stream with lower aliphatic alcohol in the presence of an acid etherification catalyst under reaction conditions effective to produce a mixture of tertiary-alkyl ethers;
   second separation means for recovering a liquid product stream rich in tertiary-alkyl ethers and recovering a light hydrocarbon fraction containing unreacted alkenes from the reaction effluent of the first reactor means along with unreacted alcohol;
   third reactor, receivably connected to said first and second separation means, comprising means for contacting the recovered light hydrocarbon and alcohol fraction from the second separation means concurrently with the second and third effluent streams from the first separation means with an acid and oxygenate conversion catalyst to convert at least a portion of said unreacted alkenes and alcohol to heavier liquid hydrocarbon product, including $C_{10}+$ distillate range hydrocarbons, aromatics and/or $C_5$–$C_9$ gasoline boiling range hydrocarbons.

2. The reactor system of claim 1 including the further means for recovering the light hydrocarbon stream in the second separation means by fractionating substantially the entire second reaction means effluent in a depentanizer or debutanizer column to provide an overhead vapor stream rich in $C_5$- or $C_4$-lower olefin and containing a minor amount of excess unreacted alcohol, and to provide a liquid product stream containing $C_5+$ liquid hydrocarbon and $C_5+$ tertiary-alkyl ether.

3. The reactor system of claim 1 wherein said olefin interconversion zone contains acidic, shape selective metallosilicate zeolite having the structure of ZSM-5 or ZSM-23.

4. A reactor system for producing liquid fuel mixtures, comprising in combination:
   interconversion reactor means for converting lower olefins to iso-alkenes and olefinic gasoline;
   etherification reactor means operably connected to said interconversion reactor means to etherify iso-alkenes therefrom;
   distillation means operably connected to said etherification reactor for separating etherification effluent;
   conversion reactor means operably connected to said distillation means and said interconversion reactor to convert distillation overhead, interconversion reactor unconverted material and said olefinic gasoline to liquid fuels.

* * * * *